(12) United States Patent
Seifert et al.

(10) Patent No.: US 11,229,531 B2
(45) Date of Patent: Jan. 25, 2022

(54) METHOD FOR CONTROLLING A DAMPING MODIFICATION

(71) Applicant: OTTO BOCK HEALTHCARE PRODUCTS GMBH, Vienna (AT)

(72) Inventors: Dirk Seifert, Vienna (AT); Roland Pawlik, Vienna (AT); Martin Seyr, Vienna (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 0 days.

(21) Appl. No.: 15/568,772

(22) PCT Filed: Apr. 15, 2016

(86) PCT No.: PCT/EP2016/058343
§ 371 (c)(1),
(2) Date: Oct. 23, 2017

(87) PCT Pub. No.: WO2016/169848
PCT Pub. Date: Oct. 27, 2016

(65) Prior Publication Data
US 2018/0085234 A1    Mar. 29, 2018

(30) Foreign Application Priority Data
Apr. 24, 2015  (DE) .......................... 102015106390.5

(51) Int. Cl.
*A61F 2/64* (2006.01)
*A61F 2/70* (2006.01)
(Continued)

(52) U.S. Cl.
CPC .................. *A61F 2/50* (2013.01); *A61F 2/64* (2013.01); *A61H 3/00* (2013.01);
(Continued)

(58) Field of Classification Search
None
See application file for complete search history.

(56) References Cited

U.S. PATENT DOCUMENTS 6,908,488 B2  6/2005 Passivaara et al.
8,801,641 B2  8/2014 Kazerooni et al.
(Continued)

FOREIGN PATENT DOCUMENTS

CA    2779784 C    5/2011
CN    1431888 A    7/2003
(Continued)

OTHER PUBLICATIONS

PCT International Search Report for PCT International Patent Application No. PCT/EP2016/058343, dated Jun. 23, 2016.

*Primary Examiner* — David H Willse
(74) *Attorney, Agent, or Firm* — Holland & Hart LLP

(57) ABSTRACT

A method for controlling a damping modification in an artificial knee joint of an orthosis, an exoskeleton, or a prosthesis. The artificial knee joint has an upper part pivotally connected to a lower part A resistance unit is secured between the upper part and the lower part in order to provide a resistance against a flexion or extension. The resistance unit is paired with an adjustment device to modify the resistance when a sensor signal of a control unit paired with the adjustment device activates the adjustment device. The flexion resistance is reduced for the swing phase. A curve of at least one load characteristic is detected when walking or standing; a maximum of the load characteristic curve when standing is ascertained; and the flexion damping is reduced to a swing-phase damping level during the standing phase when a threshold of the load characteristic below a maximum is reached.

20 Claims, 2 Drawing Sheets

(51) Int. Cl.
*A61F 2/50* (2006.01)
*A61H 3/00* (2006.01)
*A61F 2/68* (2006.01)
*A61F 2/76* (2006.01)

(52) U.S. Cl.
CPC ............ *A61F 2002/5004* (2013.01); *A61F 2002/5006* (2013.01); *A61F 2002/5033* (2013.01); *A61F 2002/6854* (2013.01); *A61F 2002/6863* (2013.01); *A61F 2002/701* (2013.01); *A61F 2002/704* (2013.01); *A61F 2002/764* (2013.01); *A61F 2002/765* (2013.01); *A61F 2002/7625* (2013.01); *A61F 2002/7635* (2013.01)

(56) References Cited

U.S. PATENT DOCUMENTS

| | | |
|---|---|---|
| 8,876,912 B2 | 11/2014 | Kampas et al. |
| 9,271,850 B2 | 3/2016 | Seyr et al. |
| 2002/0052663 A1 | 5/2002 | Herr et al. |
| 2009/0171468 A1 | 7/2009 | Pusch et al. |
| 2010/0049334 A1 | 2/2010 | Okuda et al. |
| 2011/0087339 A1 | 4/2011 | Pusch et al. |
| 2012/0215323 A1 | 8/2012 | Seyr et al. |
| 2012/0226364 A1 | 9/2012 | Kampas et al. |
| 2012/0232674 A1 | 9/2012 | Kampas et al. |
| 2014/0330393 A1 | 11/2014 | Ward et al. |
| 2014/0379096 A1* | 12/2014 | Zahedi ............ A61F 2/66 623/25 |
| 2015/0018972 A1 | 1/2015 | Albrecht-Laatsch |
| 2016/0206447 A1 | 7/2016 | Auberger et al. |

FOREIGN PATENT DOCUMENTS

| | | |
|---|---|---|
| CN | 102098986 A | 6/2011 |
| CN | 102119877 A | 7/2011 |
| CN | 102512270 A | 6/2012 |
| CN | 102740803 A | 10/2012 |
| CN | 102740805 A | 10/2012 |
| DE | 102006021802 A1 | 11/2007 |
| DE | 102008008284 A1 | 8/2009 |
| DE | 102009052887 A1 | 5/2011 |
| DE | 102009052888 A1 | 5/2011 |
| DE | 102009052890 A1 | 5/2011 |
| DE | 102009052895 A1 | 5/2011 |
| DE | 102012003369 A1 | 8/2013 |
| DE | 102013013810 B3 | 2/2015 |
| RU | 2294715 C2 | 3/2007 |
| RU | 2505272 C1 | 1/2014 |
| WO | 2011100116 A2 | 8/2011 |

\* cited by examiner

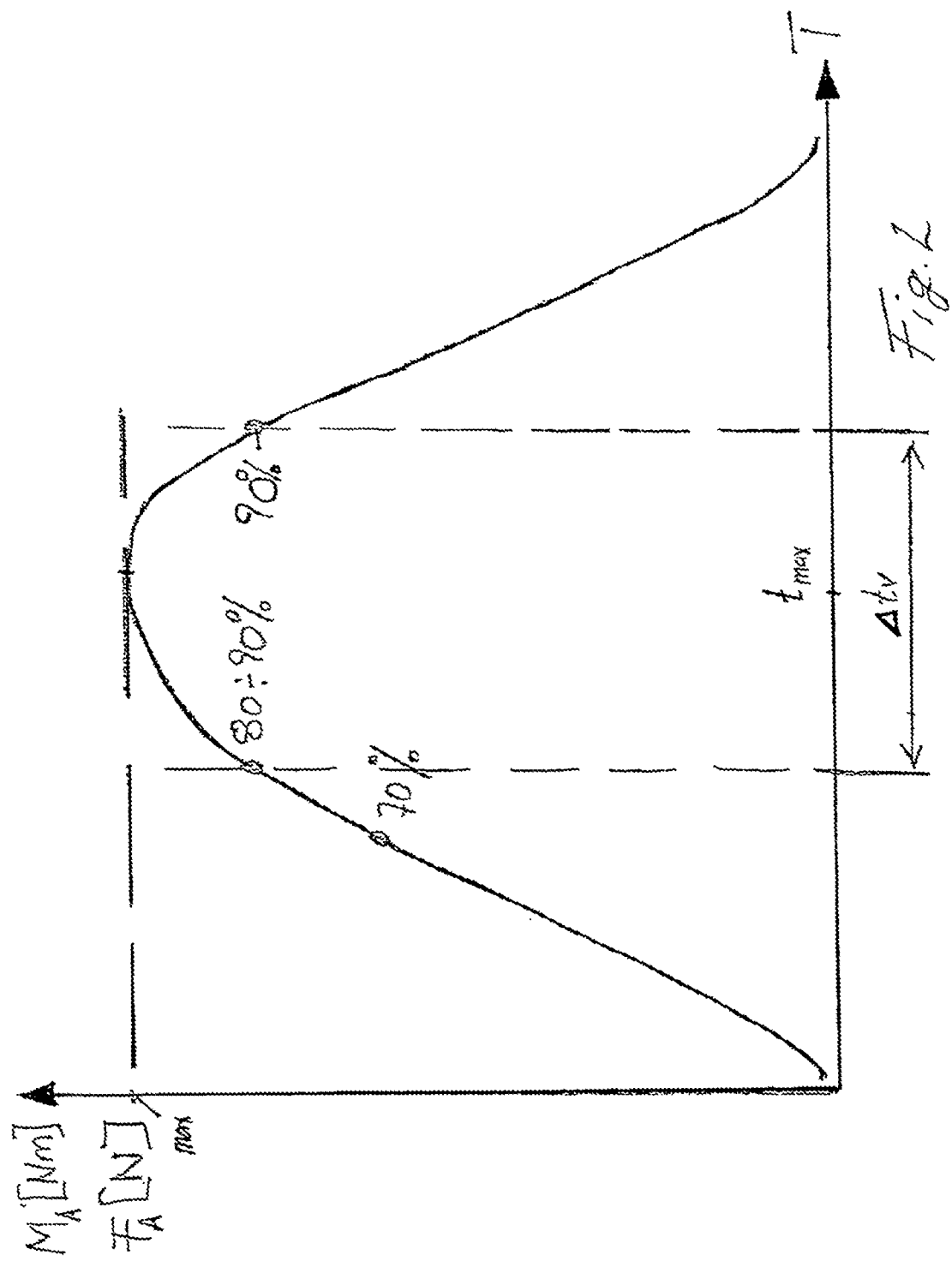

METHOD FOR CONTROLLING A DAMPING MODIFICATION

TECHNICAL FIELD

The invention relates to a method for controlling a damping variation in an artificial knee joint of an orthosis, an exoskeleton or prosthesis, wherein the artificial knee joint has an upper part and a lower part, which are fastened to one another in a manner pivotable about a pivot axis, wherein a resistance unit is fastened between the upper part and the lower part in order to provide a resistance to flexion or extension of the artificial knee joint and the resistance unit is assigned an adjustment device by means of which the resistance is varied when a sensor signal of a control unit assigned to the adjustment device activates the adjustment device, wherein the flexion resistance is reduced for the swing phase.

BACKGROUND

Knee joints for orthoses, exoskeletons or prostheses have an upper part with an upper connection part and a lower part with a lower connection part, which are connected to one another in an articulated manner. In general, receptacles for a thigh stump or a thigh brace are arranged on the upper connection part, whereas a lower leg tube or a lower leg brace are arranged on the lower connection part. In the simplest case, the upper part and the lower part are connected pivotably to one another by means of a uniaxial joint.

To be able to reproduce or support different requirements during the different phases of a step or during other movements or actions in a way that is as natural as possible, a resistance device is often provided which provides flexion resistance and extension resistance. The flexion resistance is used for setting how easily the lower part can be swung backwards in relation to the upper part when a force is applied. The extension resistance brakes the forward movement of the lower part and forms, inter alia, an extension limit stop.

DE 10 2008 008 284 A1 has disclosed an orthopedic knee joint with an upper part and with a lower part arranged pivotably thereon, which lower part is assigned multiple sensors, for example a flexion angle sensor, an acceleration sensor, an inclination sensor and/or a force sensor. The position of the extension stop is determined in a manner dependent on the sensor data.

DE 10 2006 021 802 A1 describes control of a passive prosthetic knee joint with adjustable damping in a flexion direction for adaptation of a prosthesis device with top-side connection means and with a connecting element to an artificial foot. The adaptation is made to climbing stairs, where a low-moment lifting of the prosthetic foot is detected, and the flexion damping, in a lifting phase, is lowered to below a level suitable for walking on a level surface. The flexion damping may be increased in a manner dependent on the change in the knee angle and in a manner dependent on the axial force acting on the lower leg.

DE 10 2009 052 887 A1 describes, inter alia, a method for controlling an orthotic or prosthetic joint with a resistance device and with sensors, wherein items of state information are provided by means of sensors during the use of the joint. The sensors detect moments or forces, wherein the sensor data of at least two of the determined variables are linked to one another by means of a mathematical operation, and in this way an auxiliary variable is calculated which is used as a basis for the control of the flexion and/or extension resistance.

For the purposes of controlling the damping behavior when triggering the swing phase, i.e. during the terminal stance phase for preparing the introduction of the swing phase, the flexion resistances are reduced still during the stance phase in the case of a load in the flexion direction, which may lead to a collapsing joint if it is triggered too early. The instant of triggering the swing phase, i.e. the reduction in the flexion resistance by reducing the corresponding flexion damping, is calculated, as a rule, on the basis of a normal step duration. A usual value of the step duration is assumed from the evaluation of a multiplicity of gait analyses; swing phase triggering is introduced, as a standard, on the basis of this assumed value at a certain instant after the start of the stance phase, i.e. the heel strike. Such a control is problematic if the walking speeds vary significantly or deviate from the standard. Maintaining the set standard value in the case of slow walking may lead to the swing phase triggering starting too early, i.e. the flexion resistance is reduced too strongly still during the stance phase.

SUMMARY

It is an object of the present invention to provide a method which allows flexible adaptation of a swing phase triggering with increased safety against unwanted flexion, even in the case of different gait situations or gait speeds, and under flexion load.

According to the invention, said object is achieved by means of a method having the features of the main claim. Advantageous embodiments and developments of the invention are disclosed in the dependent claims, in the description and in the figures.

The method for controlling an artificial knee joint, in particular a damping variation in an artificial knee joint of a prosthesis, an exoskeleton or orthosis, said artificial knee joint having an upper part and a lower part, which are mounted on one another in a manner pivotable about a pivot axis, wherein a resistance unit is arranged between the upper part and the lower part in order to provide a resistance to flexion or extension of the artificial knee joint and the resistance unit is assigned an adjustment device by means of which the resistance is varied when a sensor signal of a control unit assigned to the adjustment device activates the adjustment device, wherein the flexion resistance is reduced for the swing phase, provides for, when walking or standing, in particular in each step, the profile of at least one load characteristic, which acts on the orthosis or prosthesis, to be captured, a maximum of the load characteristic profile to be ascertained during the stance phase or when standing and, after reaching the maximum, the flexion damping to be reduced during the stance phase to a swing phase damping level if a threshold of the load characteristic below the maximum is reached. By introducing the swing phase triggering the reduction in the flexion resistance, connected therewith, depending on the ascertainment of a maximum of a load characteristic, it is possible to determine the instant of the swing phase triggering and hence the instant of the reduction of the flexion damping depending on the profile of the load characteristic. The flexion damping is reduced only after reaching the maximum of a load characteristic and determining that the load characteristic reduces again. The reduction in the load characteristic can be determined by sensors and the evaluation of the sensor signals about the load. Reducing the flexion damping only after the load characteristic maximum ensures that an unwanted reduction in the flexion damping does not occur before a maximum load value, which may lead to the flexion of the artificial knee joint, is reached. As a consequence, the swing phase triggering occurs adaptively; an assumption about, or estimate of, a movement duration, for example a step duration, is no longer necessary. It is possible to react variably to different sequences of motion. Both a shortened step duration and a lengthened step duration are compensated using the method according to the invention. By capturing the load characteristic when standing, it is possible to provide a swing phase triggering already from the first step; the load maximum is also ascertained when standing. The method is provided for the control both of prostheses and of orthoses and exoskeletons. Where orthoses are referred to below, the explanations likewise apply to the special form of the orthosis in the form of an exoskeleton.

In particular, the ankle moment and/or the axial force on the lower part are preferred as load characteristic. During the stance phase, a bell-shaped contour or a double-hump of the ankle moment profile and of the axial force profile over time emerges. The force which acts along the longitudinal extent of the lower part—along the longitudinal extent of the lower leg tube in the case of prostheses, along the longitudinal extent of the lower leg brace in the case of orthoses—is considered to be the axial force. If the maximum ankle moment or the maximum axial force is reached, the profile of the ankle moment or of the axial force continues to be monitored; recording the sensor data is continued over the entire step and for each step. The sensors capture or ascertain the respective load characteristic over the entire step duration, i.e. from heel strike to heel strike, and during the entire walk. If a set limit of the reducing load characteristic is reached, e.g. a value between 95% and 50% of the maximum load, the flexion damping is reduced and a swing phase triggering is introduced. Then, the resistance is reduced by activating the adjustment device. The artificial knee joint is secured for longer as a result of the swing phase triggering after reaching the maximum load characteristic. A reducing load characteristic profile is ascertained by comparison of two or more sensor values, which are captured successively in time.

The threshold for triggering the swing phase damping is variable in time and depends on the profile of the load characteristic. If the load characteristic only reduces slowly after reaching the maximum, the release is carried out later, i.e. after a longer time period has elapsed following the heel strike; if the load characteristic curve drops steeply, the swing phase triggering will occur earlier in time.

The threshold as such likewise can be set in a variable manner. The threshold depends on, for example, the walking speed or the walking situation. In the case of walking on a level surface, the threshold may lie at e.g. 90% of the maximum load or the maximum value of the load characteristic; when walking on the ramp, the swing phase triggering may occur later, for example when reaching 70% of the maximum load or 70% of the maximum value of the load characteristic, while the trigger threshold may lie at 50% of the maximum value of the load characteristic in the case of very slow walking.

The threshold may be varied depending on the walking speed. In the case of a fast walk with quick unloading, the threshold is shifted into the vicinity of the maximum value of the load characteristic, and it is shifted away from the maximum value in the case of a slow walk. Apart from the axial force or the ankle moment as a load characteristic, the roll-over speed likewise may be used as a criterion for the change in the threshold, also in addition to the ankle moment or the axial force. The quicker the lower part, i.e. the lower leg brace or the lower leg tube, is displaced from a position inclined against the moving direction into a position inclined in the walking direction, the earlier the swing phase triggering is effectuated by reducing the flexion resistance. The threshold may depend on, furthermore, the unloading speed or the speed of the drop in the characteristic. The greater the speed of the drop in the force or of the drop in the moment, i.e. the quicker there is reduction in the load characteristic, the earlier a swing phase triggering is effectuated.

A development of the invention provides for the threshold to depend on an angle position of a prosthesis component or orthosis component. By way of example, the threshold can be varied depending on a certain roll-over angle being reached. If a certain position of the lower part relative to the vertical direction is ascertained, the end of a movement cycle can be deduced. Moreover, reaching angles allows the respective walking situation to be deduced. If a full knee extension is not achieved in a step upon ground impact, the assumption can be made for example that the patient is walking up an incline or alternatively climbing stairs, and so a certain threshold which differs from a threshold for walking on a level surface is set. The same applies for the identification of a forward inclination of the lower part, or else of the upper part, as an inclination direction or absolute angle of the upper part and/or of the lower part in relation to the direction of gravity.

A development of the invention provides for the flexion damping to be reduced depending on the profile of the load characteristic. If the load characteristic reduces very quickly, the flexion damping is also reduced more quickly to a swing phase damping level during the stance phase; if there is rather a slow reduction in the load characteristic, a slow walking speed can be deduced, the latter requiring a slow reduction in the flexion damping.

The initial value of the flexion damping prior to the reduction can be set to a value or standard value which locks flexion while standing or in the stance phase. As a consequence, the starting point for a swing phase triggering with a reduction in the flexion damping in the stance phase is a locking flexion resistance such that, already from the first step, a swing phase introduction can occur by reducing the flexion damping within the scope of the terminal stance phase. The initial value of the flexion damping therefore provides a lock in the stance phase or when standing.

The reduction in the damping is effectuated continuously depending on the load variable; as a consequence, there is a direct correlation in respect of the reduction in the flexion damping and the profile of the load characteristic, in particular the reduction in the load characteristic.

As a matter of principle, the maximum of the load characteristic lies above the set threshold because otherwise it is not possible to traverse the curve of the load characteristic and activate the swing phase triggering after reaching the maximum. Thus, a threshold for the respective value of the load characteristic, which has to be reached in the first place so that the method for controlling the damping variation for triggering the swing phase is activated, is set.

The threshold for triggering the swing phase damping can be set in a variable manner and depends on the magnitude of the load characteristic or of the maximum. If only a comparatively low maximum is reached after reaching an initial threshold, the trigger threshold can vary, for example become larger, such that an earlier swing phase introduction is triggered in the case of a faster reduction in the flexion damping.

In order to provide additional safety for the patient, the flexion damping can be increased again after a reduction should the value of the load characteristic increase again. If the profile of the load characteristic passes through a change in the monotonic behavior after reaching a maximum and increases again, the flexion damping can be increased again as the assumption can be made that the usual profile of the load characteristic has been disturbed, as a consequence of which a gait behavior that deviates from the usual gait pattern is present and, as a result of which, an increased safety against unwanted flexion of the artificial joint must be provided. Such a measure serves for being able to load the artificial joint again, for example when stumbling, without it collapsing.

The resistance unit may for example be configured as an actuator, for example as a hydraulic, pneumatic, magnetorheological, magnetic, electrical, mechanical or electromagnetic resistance unit. In the case of hydraulic or pneumatic resistance units, flow transfer channels are closed, such that said flow transfer channels can no longer allow medium to flow from an extension chamber into a flexion chamber. In this way, the flow of the medium between the extension chamber and the flexion chamber can possibly also be prevented entirely. In the case of mechanical resistance devices, it is for example the case that the friction is increased to such an extent that no further flexion is possible. The same applies to electrically actuated resistance units.

Use may also be made of actuators which both actively introduce energy into the system and also conversely extract energy from the system, and thereby act as a resistance unit. Actuators may for example be formed as electric motors, hydraulic or pneumatic pumps or piezoelectric elements.

BRIEF DESCRIPTION OF THE DRAWINGS

An exemplary embodiment of the invention will be discussed in more detail below on the basis of the figures. In the figures:

FIG. 2 shows a load characteristic profile.

DETAILED DESCRIPTION

Figure 1:
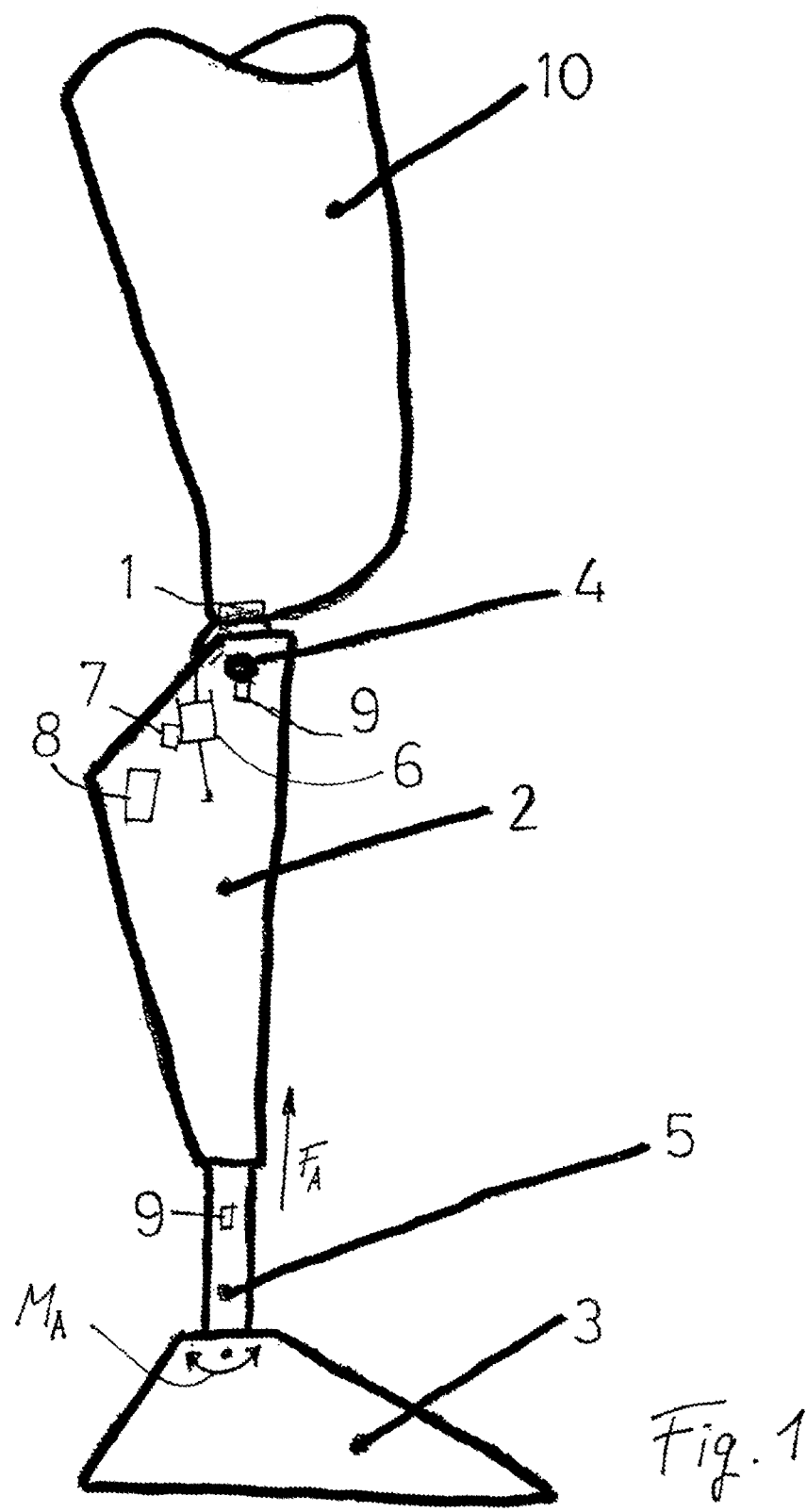
FIG. 1 shows a schematic illustration of a prosthesis.

FIG. 1 shows, in a schematic illustration, a leg prosthesis with an upper part 1 to which a thigh socket 10 for receiving a thigh stump is fastened. A lower part 2 designed as a lower leg part is arranged pivotably on the upper part 1. The lower part 2 is mounted on the upper part 1 pivotably about a pivot axis 4. The lower part 2 has a lower leg tube 5, to the distal end of which there is fastened a prosthetic foot 3 in which there may be accommodated a device for determining the axial force $A_F$ acting on the lower leg tube 5 and the ankle moment $M_A$ acting about the fastening point of the prosthetic foot 3 to the lower leg tube 5.

In or on the lower part 2 there is arranged a resistance device 6 which may be formed for example as a damper or actuator and which is supported between the upper part 1 and the lower part 2 in order to provide an adjustable extension resistance and flexion resistance. The resistance device 6 is assigned an adjustment device 7, for example a motor, a magnet or some other actuator, by means of which the respective resistance within the resistance device 6 can be varied. If the resistance device 6 is formed as a hydraulic damper or pneumatic damper, it is possible by means of the adjustment device 7 for the respective flow cross section of a flow transfer channel to be increased or decreased in size or for the flow resistance to be varied in another way. This also may be realized by opening or closing valves or changing viscosities or magnetorheological properties. If the resistance device is formed as an electric motor operating as a generator, it is possible for an increase or decrease in the respective resistances to flexion or extension to be set through variation of the electrical resistance.

To be able to activate or deactivate the adjustment device 7, a control device 8 is assigned to the lower part 2, in particular is accommodated in a lower leg cover, by means of which control device a corresponding activation or deactivation signal is output to the adjustment device 7. The adjustment device 7 is activated or deactivated on the basis of sensor data, and the sensor data are provided by one or more sensors 9 which are arranged on the artificial knee joint. These may be angle sensors, acceleration sensors and/or force sensors. The sensors 9 are connected to the control device 8, for example by cable or by means of a wireless transmission device.

The entire step cycle from the heel strike to the new, next heel strike HS, and thus also the entire swing phase with the swing phase extension and the swing phase flexion, is monitored by means of the sensors 9.

FIG. 2 shows the profile of two load characteristics, namely the ankle moment $M_A$ and the axial force $F_A$. The axial force $F_A$ acts on the lower part 2 in the direction of longitudinal extent of the lower part; the ankle moment $M_A$ acts in the region of a prosthetic foot 3 or foot part of an orthosis. The profile of the load characteristics is plotted over time T. A substantially bell-shaped profile of the load characteristics $M_A$ and $F_A$ emerges. The prior art has disclosed the reduction of the stance phase damping prior to reaching a maximum of the ankle moment $M_A$ or of the axial force $F_A$ in order to be able to effectuate a swing phase triggering. The trigger values to this end lie at 70% to 90% before reaching the maximum value $M_{Amax}$ or $F_{Amax}$ of the load characteristic. The trigger thresholds according to the prior art are determined in time and lie prior to the instant $t_{max}$, at which the maximum value of the load characteristic is present or assumed.

According to the invention, provision is now made for prompting a flexion damping reduction only after reaching the maximum $M_{Amax}$, $F_{Amax}$. To this end, the load characteristics are captured while walking at a high sampling rate by way of sensors 9 over the whole step cycle. It is likewise possible to capture angle sizes, angle speeds or position variables such as absolute angles and evaluate the profile of these characteristics. After reaching a maximum of the load characteristic or load characteristics, the flexion damping is reduced before reaching the terminal stance phase and before the toe-off in order to facilitate a flexion of the artificial knee joint and in order to be able to provide a pattern of motion that approaches natural walking. The criterion for release, i.e. a reduction in the flexion damping, consequently initially is reaching the maximum value of the load characteristic, for example the maximum ankle moment $M_{Amax}$ and/or the maximum axial force $F_{Amax}$. Subsequently, the further profile of the load characteristic is monitored or continued to be ascertained and a check is carried out as to whether a previously set but variable threshold, which is independent of the instant $t_{max}$ in time, is reached. The threshold is not determined in time but only dependent on the profile of the load characteristic. It is not necessary to quantitatively set the maximum value, just as little as it is necessary to estimate a step duration or load duration. As soon as the set threshold or the threshold that is determined on the basis of other sensor values is reached, there can be a swing phase triggering by reducing the flexion damping. For walking on a level surface, 90% of the maximum load or of the maximum moment is a usual value; however, this value depends on the walking speed, the nature of the ground underfoot and the use of walking aids. The threshold may vary between 95% of the maximum value of the load characteristic and 50% of the maximum value of the load characteristic. As a consequence, the threshold need not have a fixedly set magnitude; the manipulated variable may vary. By triggering the swing phase after reaching the maximum value of the load characteristic, the artificial knee joint is secured longer for a longer period of time, namely $\Delta t_v$. The risk of a collapsing joint as a result of an early triggering of the swing phase, for example after a delayed step, is at least reduced as a result thereof.

The unloading speed or the roll-over speed while walking can be used for setting the threshold. It is likewise possible to use the roll-over angle, the walking direction, which can be ascertained by evaluating the change in angle of the lower part in relation to the vertical direction, the quality of the angle, i.e. whether a forward inclination or a backward inclination is present, and the absolute value in space for modifying the threshold and to set the respective threshold anew while walking. As a result, a reliable swing phase triggering that is adapted to the respective walking behavior can be achieved.

In the case of fast unloading, the swing phase is triggered earlier than in the case of slow unloading, which provides increased security against unwanted flexion, particularly in the case of slow walking. All explanations relating to a prosthesis apply accordingly to an orthosis. Then, a lower leg brace is used instead of a lower leg tube. Attachment to a patient is then not effectuated by way of a shaft, but by way of belts, cuffs or the like on the leg that is present.

The invention claimed is:

1. A method for controlling a damping variation in an artificial knee joint of an orthosis, exoskeleton or prosthesis, the method comprising:
providing an artificial knee joint with an upper part and a lower part, which are fastened to one another in a manner pivotable about a pivot axis, a resistance unit fastened between the upper part and the lower part to provide a resistance to flexion or extension of the artificial knee joint, and an adjustment device assigned to the resistance unit to vary the resistance when a sensor signal of a control unit assigned to the adjustment device activates the adjustment device;
reducing the flexion resistance for a swing phase;
capturing a profile of at least one load characteristic when walking or standing, the at least one load characteristic acting on the orthosis, exoskeleton or prosthesis;
ascertaining a maximum of the at least one load characteristic profile during a stance phase or when standing;
after reaching the maximum when walking on level ground or up an incline, reducing the flexion damping during the stance phase to a swing phase damping level if a threshold of the at least one load characteristic below the maximum is reached, wherein a threshold level for triggering the swing phase damping is selected from a range between 95% and 50% of a maximum value of the at least one load characteristic.

2. The method as claimed in claim 1, wherein at least one of an ankle moment and an axial force on the lower part are used as the at least one load characteristic.

3. The method as claimed in claim 1, wherein a threshold for triggering the swing phase damping is time variable.

4. The method as claimed in claim 1, wherein a threshold for triggering the swing phase damping is set depending on at least one of a walking speed, a roll-over speed and a walking situation.

5. The method as claimed in claim 1, wherein a threshold for triggering the swing phase damping is set depending on an unloading speed.

6. The method as claimed in claim 1, wherein a threshold for triggering the swing phase damping is set depending on an angle position of a prosthesis component or orthosis component.

7. The method as claimed in claim 1, wherein the flexion damping is reduced depending on the profile of the at least one load characteristic.

8. The method as claimed in claim 1, wherein an initial value of the flexion damping prior to the reduction is set to a value which blocks flexion when standing or in the stance phase.

9. The method as claimed in claim 1, wherein the flexion damping after a reduction is increased again when a value of the at least one load characteristic increases again.

10. A method for controlling a damping variation in an artificial knee joint of an orthosis, exoskeleton or prosthesis, the method comprising:
providing an artificial knee joint with an upper part and a lower part, a resistance unit, and an adjustment device, the upper part being pivotally connected to the lower part, the resistance unit configured to apply a flexion resistance or an extension resistance, the adjustment device having a control unit, and the adjustment device configured to vary the flexion or extension resistance when a sensor signal of the control unit activates the adjustment device;
reducing the flexion resistance for a swing phase;
capturing a profile of at least one load characteristic on the orthosis, exoskeleton or prosthesis when walking or standing;
determining a maximum of the profile during a stance phase or when standing;
after reaching the maximum, reducing the flexion damping during the stance phase to a swing phase damping level if a threshold of the at least one load characteristic below the maximum is reached when each of walking on level ground, walking up an incline, and walking down a decline, wherein a threshold level for triggering the swing phase damping is selected from a range between 95% and 50% of a maximum value of the at least one load characteristic.

11. The method as claimed in claim 10, wherein at least one of an ankle moment and an axial force on the lower part are used as the at least one load characteristic.

12. The method as claimed in claim 10, wherein a threshold for triggering the swing phase damping is time variable.

13. The method as claimed in claim 10, wherein a threshold for triggering the swing phase damping is set depending on at least one of a walking speed, a roll-over speed and a walking situation.

14. The method as claimed in claim 10, wherein a threshold for triggering the swing phase damping is set depending on an unloading speed.

15. The method as claimed in claim 10, wherein a threshold for triggering the swing phase damping is set depending on an angle position of a prosthesis component or orthosis component.

16. The method as claimed in claim 10, wherein the flexion damping is reduced depending on the profile of the at least one load characteristic.

17. The method as claimed in claim 10, wherein an initial value of the flexion damping prior to the reduction is set to a value which blocks flexion when standing or in the stance phase.

18. The method as claimed in claim 10, wherein the flexion damping after a reduction is increased again when a value of the at least one load characteristic increases again.

19. A method for controlling a damping variation in an artificial knee joint of an orthosis, an exoskeleton or prosthesis, the method comprising:

providing an artificial knee joint with an upper part and a lower part, which are fastened to one another in a manner pivotable about a pivot axis, a resistance unit fastened between the upper part and the lower part to provide a resistance to flexion or extension of the artificial knee joint, and an adjustment device assigned to the resistance unit to vary the resistance when a sensor signal of a control unit assigned to the adjustment device activates the adjustment device;

reducing the flexion resistance for a swing phase;

capturing a profile of at least one load characteristic when walking or standing, the at least one load characteristic acting on the orthosis, exoskeleton or prosthesis;

ascertaining a maximum of the at least one load characteristic profile during a stance phase or when standing;

after reaching the maximum when walking on level ground or up an incline, reducing the flexion damping during the stance phase to a swing phase damping level if a threshold of the at least one load characteristic below the maximum is reached, wherein a threshold level for triggering the swing phase damping is selected from a range between 95% and 50% of a maximum value of the at least one load characteristic;

wherein an initial value of the flexion damping prior to the reduction is set to a value which blocks flexion when standing or in the stance phase.

20. The method as claimed in claim 19, wherein at least one of an ankle moment and an axial force on the lower part are used as the at least one load characteristic.

* * * * *